United States Patent
Kirnon et al.

(10) Patent No.: US 10,952,982 B2
(45) Date of Patent: Mar. 23, 2021

(54) BENEFITS OF SUPPLEMENTATION WITH N-ACETYLCYSTEINE AND GLYCINE TO IMPROVE GLUTATHIONE LEVELS

(71) Applicants: NESTEC S.A., Vevey (CH); BAYLOR COLLEGE OF MEDICINE, Houston, TX (US)

(72) Inventors: Stephen Kirnon, San Ramon, CA (US); Eric Freedland, Marblehead, MA (US); Rajagopal V. Sekhar, Missouri City, TX (US)

(73) Assignees: Societe des Produits Nestle S.A., Vevey (CH); Baylor College of Medicine, Houston, TX (US)

( * ) Notice: Subject to any disclaimer, the term of this patent is extended or adjusted under 35 U.S.C. 154(b) by 0 days.

(21) Appl. No.: 15/577,422

(22) PCT Filed: May 25, 2016

(86) PCT No.: PCT/US2016/034078
§ 371 (c)(1),
(2) Date: Nov. 28, 2017

(87) PCT Pub. No.: WO2016/191468
PCT Pub. Date: Dec. 1, 2016

(65) Prior Publication Data
US 2018/0161297 A1 Jun. 14, 2018

Related U.S. Application Data

(60) Provisional application No. 62/167,433, filed on May 28, 2015.

(51) Int. Cl.
| | | |
|---|---|---|
| *A61K 31/198* | (2006.01) | |
| *A61K 38/05* | (2006.01) | |
| *A61K 31/167* | (2006.01) | |
| *A61K 31/223* | (2006.01) | |
| *A61K 31/341* | (2006.01) | |
| *A61K 38/21* | (2006.01) | |
| *A61K 31/683* | (2006.01) | |
| *A61K 31/27* | (2006.01) | |
| *A61K 45/06* | (2006.01) | |
| *A61K 31/381* | (2006.01) | |
| *A61K 31/205* | (2006.01) | |
| *A23K 20/142* | (2016.01) | |
| *A23K 50/50* | (2016.01) | |
| *A61P 21/00* | (2006.01) | |
| *A61P 39/00* | (2006.01) | |
| *A61P 31/18* | (2006.01) | |
| *A61P 29/00* | (2006.01) | |
| *A61K 38/02* | (2006.01) | |

(52) U.S. Cl.
CPC .......... *A61K 31/198* (2013.01); *A23K 20/142* (2016.05); *A23K 50/50* (2016.05); *A61K 31/167* (2013.01); *A61K 31/205* (2013.01); *A61K 31/223* (2013.01); *A61K 31/27* (2013.01); *A61K 31/341* (2013.01); *A61K 31/381* (2013.01); *A61K 31/683* (2013.01); *A61K 38/02* (2013.01); *A61K 38/05* (2013.01); *A61K 38/21* (2013.01); *A61K 45/06* (2013.01); *A61P 21/00* (2018.01); *A61P 29/00* (2018.01); *A61P 31/18* (2018.01); *A61P 39/00* (2018.01)

(58) Field of Classification Search
CPC ....... A61K 31/198; A61K 38/05; A61P 21/00; A61P 9/00–14; A61P 15/00; A61P 15/08; A61P 19/10; A61P 21/06; A61P 27/00; A61P 27/16; A61P 37/04; A23L 33/175; A23L 33/18
See application file for complete search history.

(56) References Cited

U.S. PATENT DOCUMENTS

| | | | | |
|---|---|---|---|---|
| 5,792,110 A | * | 8/1998 | Cunningham .......... | A61M 5/46 604/158 |
| 7,175,587 B2 | * | 2/2007 | Gordon .................... | A61N 2/02 600/9 |
| 7,227,001 B2 | * | 6/2007 | Anziano ................ | C07K 16/40 530/387.1 |
| 7,351,427 B2 | * | 4/2008 | Hassan .................. | A61K 9/127 424/450 |
| 7,754,700 B2 | * | 7/2010 | Trager ................. | A61K 31/185 424/638 |
| 8,697,679 B2 | * | 4/2014 | Hageman ................ | A23L 33/30 514/183 |

(Continued)

FOREIGN PATENT DOCUMENTS

| | | | | |
|---|---|---|---|---|
| WO | 03047558 | | 6/2003 | |
| WO | WO-03047558 A2 | * | 6/2003 | ............. A61K 31/00 |

OTHER PUBLICATIONS

Neustadt (Medication-induced mitochondrial damage and disease, Mol. Nutr. Food Res. 2008, 52:780-788) (Year: 2008).*

(Continued)

*Primary Examiner* — Jeffrey E. Russel
(74) *Attorney, Agent, or Firm* — K&L Gates LLP

(57) ABSTRACT

The present invention concerns compositions and methods related to utilizing glycine and N-acetylcysteine for a variety of medical conditions (e.g., muscle loss such as sarcopenia, HIV infection and others, organ damage such as those from diabetes and insulin resistance and diabetic nephropathy, cardiac function and failure such as preventing or improving heart failure, fatty liver, cancer prevention, and others) related to reduced levels of glycine, N-acetylcysteine, and/or glutathione.

6 Claims, 6 Drawing Sheets

(56) References Cited

U.S. PATENT DOCUMENTS

| | | | |
|---|---|---|---|
| 8,747,894 B2* | 6/2014 | Stroppolo | A61K 9/2009 424/466 |
| 8,911,724 B2* | 12/2014 | Kaiser | A61K 31/198 424/641 |
| 2002/0136763 A1* | 9/2002 | Demopoulos | A61L 2/16 424/451 |
| 2002/0142991 A1 | 10/2002 | Herzenberg et al. | |
| 2004/0022841 A1 | 2/2004 | Hassan et al. | |
| 2004/0106591 A1 | 6/2004 | Pacioretty et al. | |
| 2004/0120983 A1* | 6/2004 | Connolly | A61K 31/00 424/439 |
| 2006/0116334 A1* | 6/2006 | Hendrix | A61K 45/06 514/27 |
| 2006/0160721 A1* | 7/2006 | Pownall | A61K 31/00 514/1.9 |
| 2010/0099762 A1* | 4/2010 | Bush | A61K 31/496 514/546 |
| 2011/0077303 A1* | 3/2011 | Sekhar | A61K 31/198 514/562 |
| 2012/0302816 A1* | 11/2012 | Tour | A61P 31/00 600/1 |
| 2013/0183277 A1 | 7/2013 | Kaiser | |
| 2013/0203753 A1* | 8/2013 | Cundy | A61P 25/16 514/231.8 |
| 2013/0266545 A1* | 10/2013 | McCord | A61K 31/198 424/93.7 |
| 2014/0045874 A1* | 2/2014 | Tolleth | A61K 31/375 514/276 |
| 2014/0288177 A1* | 9/2014 | Sekhar | A61K 31/198 514/562 |
| 2014/0303080 A1* | 10/2014 | Yu | A61K 8/64 514/7.3 |
| 2014/0328753 A1* | 11/2014 | Clofent-Sanchez | A61K 49/0002 424/1.49 |
| 2017/0281713 A1* | 10/2017 | Crum | A61K 31/095 |

OTHER PUBLICATIONS

Tchiakpe (The Prediction of Integrase Inhibitors Efficacy in Third Line Regimen after First and Second Line Antiretroviral Therapy Failure in Senegal, J Antivir Antiretrovir 2014, 6:127-134) (Year: 2014).*

Bar-Shai (Reactive nitrogen species induce nuclear factor-κB-mediated protein degradation in skeletal muscle cells, FRBM 2006, 40:2112-2125) (Year: 2006).*

Tchiakpe (The Prediction of Integrase Inhibitors Efficacy in Third Line Regimen after First and Second Line Antiretroviral Therapy Failure in Senegal, J Antivir Antiretrovir 2014, 6:127-134, of record) (Year: 2014).*

Nguyen et al. Effect of Increasing Glutathione With Cysteine and Glycine Supplementation on Mitochondrial Fuel Oxidation, Insulin Sensitivity, and Body Composition in Older HIV-Infected Patients. The Journal of Clinical Endocrinology and Metabolism. Jan. 2014, vol. 99, No. 1, pp. 169-177. (Year: 2014).*

Borges-Santos et al., "Plasma Glutathione of HIV+ Patients Responded Positively and Differently to Dietary Supplementation with Cysteine or Glutamine", Nutrition, vol. 28, Issue No. 7, Jul. 2012, pp. 753-756, XP028926867.

Ruiz-Ramirez et al., "Glycine Restores Glutathione and Protects Against Oxidative Stress in Vascular Tissue from Sucrose-fed Rats", Clinical Science, vol. 126, Issue No. 1, 2014, pp. 19-29, XP-002787390.

* cited by examiner

US 10,952,982 B2

BENEFITS OF SUPPLEMENTATION WITH N-ACETYLCYSTEINE AND GLYCINE TO IMPROVE GLUTATHIONE LEVELS

CROSS REFERENCE TO RELATED APPLICATIONS

The present application is a National Stage of International Application No. PCT/US2016/034078, filed on May 25, 2016, which claims priority to U.S. Provisional Patent Application No. 62/167,433, filed on May 28, 2015, the entire contents of which are being incorporated herein by reference.

TECHNICAL FIELD

The present disclosure is directed at least to the fields of biochemistry, cell biology, chemistry, molecular biology, and medicine.

BACKGROUND

The free radical theory of aging suggests that the biological process of aging results in increased oxidative stress in elderly humans. The ability of a cell to resist the damaging potential of oxidative stress is determined by a vital balance between generation of oxidant free radicals and the defensive array of antioxidants available to the cell. There are multiple antioxidant defense systems and of these, glutathione (GSH) is the most abundant intracellular component of overall antioxidant defenses. GSH, a tripeptide, is synthesized from precursor amino-acids glutamate, cysteine, and glycine in two steps catalyzed by glutamate cysteine ligase (GCL, also known as γ-glutamylcysteine synthetase, EC 6.3.2.2) and γ-L-glutamyl-L-cysteine:glycine ligase (also known as glutathione synthetase, EC 6.3.2.3), and GSH synthesis occurs de novo in cells.

Glutathione deficiency has been implicated in several diseases in humans including diabetes, HIV infection, protein energy malnutrition in children, sickle-cell anemia, infection, neurological disorders such as Parkinson's disease, liver disease and cystic fibrosis. Evidence from several animal (Stohs et al., 1984; Farooqui et al, 1987; Liu et al., 2000) and human studies (Al-Turk et al., 1987; Matsubara et al., 1991; Lang et al., 1992; Samiec et al., 1998; Erden-Inal et al., 2002; Loguercio et al., 1996) suggest that concentrations of glutathione also decline with aging. GSH deficiency in aging is associated with an increased pro-oxidizing shift (Rebrin, 2008) leading to increased oxidative stress (Rikans and Hornbrook, 1997). These changes have been implicated in diseases of aging such as cataracts (Campisi et al., 1999; Castorina et al., 1992; Sweeney et al., 1998), age-related macular degeneration (Samiec, 1998), altered immune function (Fidelus and Tsan, 1987; Furukawa et al., 1987) and neurodegenerative disease (Liu et al., 2004), and in increased DNA damage (Hashimoto et al., 2008) at a molecular level. While the underlying mechanisms for aging-associated glutathione deficiency is not well understood, there are suggestions that perturbations in glutathione synthesis could be involved (Toroser and Sohal, 2007).

Other and further objects, features, and advantages will be apparent from the following description of the presently preferred embodiments of the invention, which are given for the purpose of disclosure.

SUMMARY

Embodiments of the disclosure concern methods and/or compositions for treating or preventing or delaying onset of a medical condition or physical state in which reduced levels of intracellular GSH is directly or indirectly related. Embodiments of the disclosure also concern methods and/or compositions for treating or preventing or delaying onset of a medical condition or physical state in which reduced blood or intracellular levels of cysteine and/or glycine is directly or indirectly related. In specific embodiments, the level of intracellular GSH in an individual is increased, upon which the medical condition or physical state is thereby treated, prevented, or had a delay in onset. In certain embodiments, the level of C-reactive protein (CRP) in an individual is reduced, upon which the medical condition or physical state is thereby treated, prevented, or had a delay in onset.

In particular embodiments, methods are contemplated that provide benefits from glutathione, n-acetylcysteine and/or glycine, and in specific cases there is a contribution from each of glutathione, n-acetylcysteine and/or glycine individually and/or collectively.

In one embodiment of the disclosure, there is a method of producing increased blood levels of cysteine and glycine (e.g. cysteinylglycine) (or functional derivatives thereof) in an individual in need thereof to increase intracellular GSH levels. The individual may be known to have a medical condition or physical state that would benefit from increased GSH levels, or the individual may be suspected of having a medical condition or physical state that would benefit from increased GSH levels. In particular embodiments, the individual subjected with methods and/or compositions of the invention is desiring prevention of one or more undesirable physical states (or the effects thereof, such as with aging) or medical conditions. In certain embodiments, an individual is provided effective levels of cysteine and glycine or functional derivatives thereof for the explicit purpose of increasing GSH levels to treat, prevent, or delay the onset of a medical condition or physical state.

In particular embodiments, an individual is identified as needing treatment (or prevention or delay of onset) of a medical condition related to insufficient GSH levels.

Embodiments of the disclosure concern a variety of methods for the treatment or prevention or delay of onset of one or more medical conditions or physical state related to insufficient levels of glutathione in one or more cells of an individual. In specific embodiments are methods for the treatment or prevention or delay of onset of one or more medical conditions or physical state related to insufficient concentrations of glycine and/or cysteine intracellularly. In specific aspects, methods allow for the treatment or prevention or delay of onset of one or more medical conditions or physical states because of the inherent benefits of restoring intracellular concentrations of glycine and/or cysteine independent of GSH. In specific embodiments, the condition or physical state includes at least one or more of the following: muscle loss (for any reason, including at least sarcopenia, HIV infection, aging and/or cachexia, deleterious effects of weightlessness; organ damage (for example, from diabetes and insulin resistance and including diabetic nephropathy); cardiac function and failure (for example, preventing or improving heart failure and/or improving cardiac contractile function); fatty liver; cancer prevention; fetal metabolic programming for prevention of later development of obesity and/or diabetes; maternal and fetal health in gestational diabetes; exercise capacity and physical function; obesity; quality of life; longevity; neurodegenerative disease; prophylaxis for preventing nephropathy in individuals undergoing contrast studies or procedures or HIV associated neuropathy prevention for acetaminophen toxicity; non-alcoholic steatohepatitis; non-alcoholic fatty liver disease (including with or without inflammation); tinnitus; dizziness; alcohol hangover; hearing impairment Alzheimer's; Parkinson's Disease; osteoporosis, hypertension, atherosclerosis/coronary artery disease, and myocardial damage after stress, such as from burns or trauma; cystic fibrosis; non-alcoholic fatty liver disease; inflammation; improving memory and cognition; post-traumatic recovery and survival (e.g., post-surgical, post-sepsis, post-blunt or penetrating trauma due to accident or physical assault, etc.); traumatic brain injury (including concussions); improve recovery from general trauma and surgery; diabetes prevention; treatment or prevention of pre-diabetes/metabolic syndrome; and so forth.

In one embodiment, there is a method of preventing and/or treating sarcopenia, sarcopenic obesity, or cachexia. In specific embodiments for cachexia, the cachexia is present in the individual because of an underlying medical condition, such as being chronically ill, having HIV, having cancer, having COPD, aging in otherwise healthy individuals (sarcopenia) and so forth. In specific embodiments for older HIV patients, supplementation with compositions contemplated herein boost glutathione and result in increased lean mass (muscle) and decreased fat mass.

A particular embodiment of the disclosure provides for the prevention and/or treatment of an eye condition resulting directly or indirectly from low GSH levels, including low levels in the lens of the eye that is known for being rich in glutathione. Such conditions include cataracts and/or glaucoma, presbyopia (loss of near vision with aging requiring reading glasses). Or presbyacusis (loss of hearing with aging, requiring hearing aids), for example.

In a certain embodiment, there is a method of preventing and/or treating inflammation of any kind, and in specific embodiments the method involves lowering of C reactive protein (CRP; an inflammation marker or a decline in TNF-alpha, such as in HIV patients In specific embodiments, the inflammation is related to a response to harmful stimuli, including one or more pathogens, damaged cells, and/or irritants. The inflammation may be acute or chronic. In some cases, the inflammation is associated with a disorder, such as aging, diabetes, acne, asthma, autoimmune disease, celiac disease, prostatitis, glomerulonephritis, inflammatory bowel disease, pelvic inflammatory disease, reperfusion injury, rheumatoid arthritis, sarcoidosis, transplant rejection, vasculitis, interstitial cystitis, atherosclerosis, allergies, myopathies, leukocyte defects, drug reaction (such as cocaine or ecstasy), cancer, depression, muscle repair, and so forth. It is recognized that inflammation is associated with immunity, and in specific embodiments there are methods of providing individuals that are receiving vaccines with NAC and Glycine to enhance the immune response to vaccines.

In particular embodiments, methods of the disclosure prevent and mitigate/treat mitochondrial toxicity, including drug-induced mitochondrial toxicity. For example, individuals with HIV and receiving antiretroviral HIV medications that are deleterious to mitochondrial function are provided effective amounts of NAC and Glycine to improve mitochondrial function.

In a specific embodiment, there is a method of preventing and/or treating acetaminophen toxicity. In particular, an individual that will intake acetaminophen or that is taking acetaminophen or that has acetaminophen toxicity is provided effective levels of one or more compositions as contemplated herein. The individual with acetaminophen toxicity may or may not be a chronic user of acetaminophen. In specific embodiments, the individual consumes acetaminophen at the same time as consuming one or more agents that increases GSH levels in the individual.

In particular embodiments, there is a method of improving muscle performance and recovery, such as from muscle stress, including that muscle stress associated with exercise. In specific embodiments, the individual is an athlete although the individual may not be an athlete. The individual may engage in exercise for recreational and/or health purposes. The individual may take one or more agents that increases GSH levels in the individual before, during, and/or after the exercise (including before and/or after and within minutes, hours, or days before and/or after the exercise). The individual may take one or more agents that raise intracellular levels of cysteine and/or glycine in the individual before, during, and/or after the exercise (including before and/or after and within minutes, hours, or days before and/or after the exercise). In specific embodiments, raising intracellular NAC and/or glycine enhances muscle performance and/or recovery independent of its effects on GSH. The exercise may be of any kind, including aerobic ("cardio") exercise and/or weight training, for example. The individual may have a medical condition or physical state that directly or indirectly is associated with reduced levels of GSH. In specific embodiments, the individual is an older individual with HIV, such as an individual that is 50 years of age or older. Studies indicate that older HIV patients having received compositions as contemplated herein significantly increased muscle strength in both hands in 2 weeks.

Embodiments of the disclosure include methods for treating, preventing, or delaying the onset of accelerated aging in non-elderly individuals; the accelerated aging may before any reason, including at least as with HIV infection or those exposed to zero gravity for any period of time. In certain embodiments, there is reversal of accelerated aging (such as is seen with HIV, weightlessness, or the presence of age-related deficiencies (functional decline, loss of muscle strength, decreased quality of life, cataract formation, immunosenescence), such as is normally seen in non-HIV people (around 70-80 years of age) at a far younger age (50 years or younger) in HIV-infected patients). In a certain embodiment, there is a method of increasing longevity in an individual. In specific embodiments, the individual is at least 50, 55, 60, 65, 70, 75, 80, 85, 90, or 95 years old. In certain embodiments of the disclosure, longevity is increased in an individual that is provided an effective amount of glycine and n-acetylcysteine. Thus, in particular embodiments of the invention there are methods and compositions related to increasing lifespan of an individual. The individual may or may not have life-threatening medical conditions. In cases of weightlessness, such as with individuals experiencing zero gravity, there may be muscle atrophy and/or osteopenia, and so forth.

In certain embodiments, there is improvement of cognitive function in an individual, including for an individual that does not have detectable impairment of cognitive function or for an individual that has detectable impairment of cognitive function, including impairment for any reason. In specific embodiments, the methods allow a delay of the onset of cognitive dysfunction or the enhancement of normal cognitive function. Cognitive function may be defined as the mental process of knowing, including aspects such as awareness, perception, reasoning, and judgment, including but not limited to that which comes to be known, as through perception, reasoning, or intuition; knowledge. In specific embodiments, compositions as contemplated herein are provided to an individual to improve memory, including in an individual with normal or impaired memory.

Embodiments of the disclosure include methods of improvement of skeletal muscle loss that occurs for any reason, including for cachexia, sarcopenia, inactivity, stress (including post-surgical, sepsis, and post-trauma); and so forth. The improvement may be a reduction in the rate or amount of muscle loss and/or a reversal of muscle loss.

In one embodiment, there is prophylaxis for preventing or treating nephropathy, at least, for example, in individuals undergoing contrast studies or procedures or that has diabetes and/or HIV. The nephropathy may be damage to or disease of a kidney, and the nephropathy may be non-inflammatory or inflammatory. Examples of nephropathies include deposition of the IgA antibodies in the glomerulus, administration of analgesics, xanthine oxidase deficiency, toxicity of chemotherapy agents or other drugs, long-term exposure to lead or its salts; systemic lupus erythematosus, trauma, post-obstructive uropathy, nephritis; nephrotic syndrome; diabetes mellitus and high blood pressure (hypertension), which lead to diabetic nephropathy and hypertensive nephropathy.

In certain embodiments of the invention, the present invention concerns compositions and methods related to utilizing glycine and n-acetylcysteine (NAC) for therapeutic and/or preventative indications in mammals in need thereof. The mammals can be of any kind and can include humans, dogs, cats, horses, pigs, sheep, and goats, for example. In certain embodiments, the present invention is directed to one or more methods and/or compositions that concern impaired glutathione turnover and/or increased oxidative stress and/or oxidant damage in a mammal, including such impaired glutathione turnover and/or increased oxidative stress and/or oxidant damage in aging or diabetes. In specific embodiments, the present invention concerns beneficial effects of comestibles (including at least dietary supplements) with glycine and n-acetylcysteine in a mammal in need thereof, including one that is aging or has diabetes, for example.

A mammal in need thereof can include one that needs prevention or treatment of deleterious effects of aging or that needs prevention or treatment of diabetes or complications from diabetes or that needs prevention or treatment from one or more of the following: dyslipidemia; insulin resistance; obesity; fatty acid oxidation; diabetic dyslipidemia; diabetic microvascular complications (for example, nephropathy, retinopathy, and/or neuropathy); high cholesterol and/or triglyceride levels; fatty liver disease; neurodegenerative disease in aging; statin-induced myopathy.

In some embodiments, the present invention concerns individuals, for example elderly humans, that have decreased GSH levels for any reason, including because of diminished synthesis, and in certain embodiments it is diminished because of poor availability of precursor amino acids, for example. A low GSH state predisposes an individual to increased oxidative stress, measured by plasma markers of oxidative damage, for example. Supplementation with both NAC and glycine results in improved GSH synthesis and concentrations, and decreases in plasma markers of damage, in certain embodiments of the invention, and in particular aspects of functional derivatives of NAC and glycine are effective. GSH improvement through increased synthesis can impact improvement on at least metabolic health, including mitochondrial fuel metabolism, insulin resistance, body composition and muscle strength. This can be achieved by increasing the availability of the precursors cysteine and glycine by administering them in their various forms and precursors, which include at least N-acetylcysteine (NAC), L-glycine, L-glycine ethyl ester, and dipeptide forms, e.g., cysteinylglycine or n-acetylcysteinylglycine. In certain embodiments, NAC and/or glycine supplementation results in improvements on at least metabolic health, including mitochondrial fuel metabolism, insulin resistance, body composition and muscle strength, and this occurs independent of GSH.

In one embodiment of the invention, there are methods and compositions that are useful for reducing and/or preventing oxidative stress in an individual. In a specific embodiment, the methods and compositions are useful for treating and/or preventing medical conditions associated with oxidative stress. In a particular embodiment, the methods and compositions of the invention are useful for treating and/or preventing medical conditions associated with reduced levels of glutathione. In one specific embodiment of the invention, the methods and compositions are useful for treating diabetes. In a certain aspect of the invention, the methods and compositions are useful for providing to the elderly. In particular cases, the present invention provides methods and compositions useful for aging.

In certain embodiments, the invention concerns compositions and the following exemplary method(s): method to reduce plasma F2-isoprostane levels; method to reduce plasma F3-isoprostane and/or F2-isoprostane levels and/or neuroprostanes and/or F4-isoprostane levels (for example, as it relates to a marker for brain oxidative stress); method to increase GSH production; method to increase GSH intracellular concentration; method to increase liver (and separately, muscle, for example) GSH levels; method to improve insulin sensitivity; method to increase fat oxidation; method to reduce body weight; method to treat/prevent dyslipidemia; method to treat/prevent fatty liver disease and/or lowering excess fat content in the liver; method to lower cholesterol level; method of preventing myopathy, including statin induced myopathy; and/or method to lower triglyceride level.

In one embodiment of the invention, there is a composition consisting essentially of glycine and N-acetylcysteine. In another embodiment of the invention, there is a composition consisting of glycine and n-acetylcysteine.

In certain aspects, there is a method of increasing GSH production in an individual, comprising the step of providing an effective amount of glycine and n-acetylcysteine to the individual.

In certain embodiments of the disclosure, because aging is associated with impaired fat oxidation and obesity, and also with glutathione deficiency due to impaired synthesis, providing glycine and n-acetylcysteine restores glutathione synthesis and concentrations, and also improves fat oxidation, insulin resistance, obesity, and/or dyslipidemia.

In specific embodiments, there is a method for preventing and/or treating a hangover from alcohol ingestion using compositions encompassed in the disclosure. The hangover may, in specific embodiments, be caused directly or indirectly by depletion of GSH stores or by interaction of acetaldehyde with GSH and/or cysteine, resulting in their depletion. In some embodiments, the hangover is directly or indirectly because of an excess of congeners, including a number of substances such as amines, acetones, acetaldehydes, histamines, and tannins, and particularly those that are toxic. The alcohol may be of any kind, including liquor (dark or light), beer, and/or wine. In particular embodiments, the restoration of cellular healthy glutathione levels protects against oxidative stress, offsets the effects of acetaldehyde, and protects against hangover or reduces its deleterious effects.

In specific embodiments, there is a method for preventing and/or treating polycystic ovary syndrome (PCOS) in an individual employing compositions contemplated herein. In particular embodiments, the method directly or indirectly addresses excess insulin (caused for any reason) that affects the ovaries by increasing androgen production, which interferes with the ovaries' ability to ovulate. In some embodiments, the method for preventing and/or treating PCOS addresses low-grade inflammation that stimulates polycystic ovaries to produce androgens.

In particular embodiments, effective amounts of glycine or a functional derivative thereof and N-acetylcysteine or a functional derivative thereof are provided to an individual to enhance immunity following vaccination. In specific embodiments, in the absence of providing the glycine (or functional derivative thereof) and N-acetylcysteine (or functional derivative thereof), the vaccination would elicit a reduced level of immunity compared to providing the vaccine when the individual has been given the compositions. In specific embodiments, correcting glutathione with glycine/NAC permits an enhanced chance for vaccinations to be successful, especially in those populations whose innate immune cells are poorly functional (immunosenescent populations such as geriatric older people, and HIV infected patients, for example). Vaccine failure rates are typically higher in these populations, and glycine/NAC overcomes such deficiencies, in specific embodiments. In specific embodiments, an individual is given glycine/NAC ahead of the vaccine, at the time of the vaccine, and/or after the vaccine. In specific embodiments, the individual receives glycine/NAC on the order of months, weeks, or days prior to the vaccine. In certain cases, the individual is given glycine/NAC for 1, 2, 3, or 4 weeks prior to the vaccine. In certain embodiments, the individual receives glycine/NAC on the order of months, weeks, or days after the vaccine. In specific embodiments, the individual is given glycine/NAC for 1, 2, 3, or 4 weeks after the vaccine. In certain embodiments, there is a method for treating hearing loss in an individual or preventing hearing loss in an individual susceptible thereto by providing an effective amount of glycine and/or NAC (or functional derivatives thereof). In specific embodiments, the individual is susceptible to hearing loss because of aging, loud noise, head trauma, infection, disease, genetic condition, malformality, a combination thereof, and so forth. The hearing loss may be partial or complete, and one or both ears may be affected.

In certain embodiments, there is a method for treating traumatic brain injury (TBI—acute and chronic conditions due to TBI) and/or concussion or preventing traumatic brain injury (TBI—acute and chronic conditions due to TBI) and/or concussion in an individual in need thereof. The TBI or concussion may be the result of an accident, trauma, and so forth. In specific embodiments of the method, an effective amount of glycine and/or NAC (or functional derivatives thereof) are provided to the individual prior to onset of the TBI and/or concussion and/or after its onset.

In particular embodiments, ototoxicity (e.g., due to drugs, e.g., antibiotics, aminoglycosides, loop diuretics, platinum-based chemotherapy agents (such as cisplatin), nonsteroidal anti-inflammatory drugs), tinnitus, vertigo, dizziness, and/or Meniere's Disease are treated or prevented in an individual by providing an effective amount of glycine and/or NAC (or functional derivatives thereof). The condition may be reversible and temporary or irreversible and permanent in the absence of the glycine and/or NAC (or functional derivatives thereof).

In certain embodiments, compositions of the disclosure are beneficial to lipid metabolism in the liver. Benefits may stem from glutathione, n-acetylcysteine and/or glycine and in specific embodiments there is a contribution from each of these components individually and/or collectively.

In embodiments of the disclosure, the methods and/or compositions are utilized in any mammal, including human, horse, dog, cat, goat, sheep, cow, pig, and so forth.

In one embodiment, there is a method of treating an individual for one or more medical conditions or physical states, comprising the step of providing to the individual an effective amount of a composition comprising glycine or a functional derivative thereof and N-acetylcysteine or a functional derivative thereof, wherein the medical condition or physical state is selected from the group consisting of: (a) muscle loss; (b) deleterious effects of weightlessness; (c) organ damage; (d) cardiac function or failure; (e) cancer prevention; (f) fetal metabolic programming for prevention of later development of obesity and/or diabetes; (g) maternal and fetal health in gestational diabetes; (h) exercise capacity and physical function; (i) obesity; (j) longevity; (k) Hepatotoxicity; (l) neurodegenerative disease; (m) prophylaxis for nephropathy; (n); prevention for acetaminophen toxicity; (o) non-alcoholic steatohepatitis (NASH); (p) alcohol hangover; (q) hearing impairment; (r) Alzheimer's Disease; (s) Parkinson's Disease; (t) osteoporosis; (u) hypertension; (v) polycystic ovary syndrome (PCOS); (w) atherosclerosis; (x) coronary artery disease, (y) myocardial damage after stress; (z) insufficient immunity following vaccination; (aa) cystic fibrosis; (bb) traumatic brain injury; (cc) concussion; (dd) ototoxicity (ee) tinnitus; (ff) vertigo; (gg) dizziness; (hh) Meniere's Disease; (ii) post-trauma recovery and survival; (jj) non-alcoholic fatty liver disease (NAFLD); (kk) neurocognitive function; and (ll) a combination thereof.

In specific embodiments, the glycine or functional derivative thereof and the N-acetylcysteine or functional derivative thereof are provided to the individual in the same composition or different compositions. The glycine or functional derivative thereof and the N-acetylcysteine or functional derivative thereof may be provided orally to the individual.

In particular embodiments, the glycine derivative is selected from the group consisting of D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)—N-Boc-(2'-chlorophenyl)glycine; Boc-L-cyclopropylglycine; Boc-L-cyclopropylglycine; (R)—N-Boc-4-fluorophenylglycine; Boc-D-propargylglycine; Boc-(S)-3-thienylglycine; Boc-(R)-3-thienylglycine; D-α-Cyclohexylglycine; L-α-Cyclopropylglycine; N-(2-fluorophenyl)-N-(methylsulfonyl) glycine; N-(4-fluorophenyl)-N-(methylsulfonyl)glycine; Fmoc-N-(2,4-dimethoxybenzyl)-Gly-OH; N-(2-Furoyl)glycine; L-α-Neopentylglycine; D-Propargylglycine; sarcosine; Z-α-Phosphonoglycine trimethyl ester, and a mixture thereof. The glycine and N-acetylcysteine may be comprised in a dipeptide, such as N-acetylcysteinylglycine or cysteinylglycine, for example.

In one embodiment, there is a method of neutralizing or mitigating a drug-induced mitochondrial dysfunction or impairment for an individual, comprising the step of providing to the individual an effective amount of a composition comprising glycine or a functional derivative thereof and N-acetylcysteine or a functional derivative thereof. In a specific embodiment, the drug-induced mitochondrial dysfunction of impairment is from an antiviral drug, such as wherein the antiviral drug is for HIV or hepatitis. In a specific embodiment, the drug is an anticonvulsant; psychotropic (Antidepressant; Antipsychotic; Barbiturate; Anxiety medication); Cholesterol medication; Analgesic/anti-inflammatory drug; Antibiotic; Anti-arrhythmic drug; Steroid;

Anti-viral drug; Anti-retroviral drug; Cancer medication; Diabetes medication; Beta-blocker; or is an immunization. The drug may be Valproate (Depakote); Amitriptyline (Elavil); Amoxapine; Fluoxetine (Prozac); Citalopram (Cipramil); Clorpromazine (Thorazine); Fluphenazine (Prolixin); Haloperidol (Haldol); Resperidone (Risperdol); Phenobarbital; Secobarbital (Seconal); Butalbital (Fiornal); Ambarbital (Amytal); Pentobarbital (Nembutal); Alprazolam (Xanax); Diazepham (Valium, Diastat); Statins; Bile acids-cholestryamine; Ciprofibrate; ASA (Aspirin); Acetaminophen (Tylenol); Indomethacin (Indocin); Naproxen (Aleve); Diclofenac; Tetracycline, minoclycline; Chloramphenical; Aminoglycosides; Linozolid (Zyvox); Amiodarone; Interferon; Zidovudine; Doxorubicine (Adriamycin); Cis-platinum; Tamoxifen; Metformin; or a mixture thereof.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

DETAILED DESCRIPTION

I. Definitions

Figure 1:
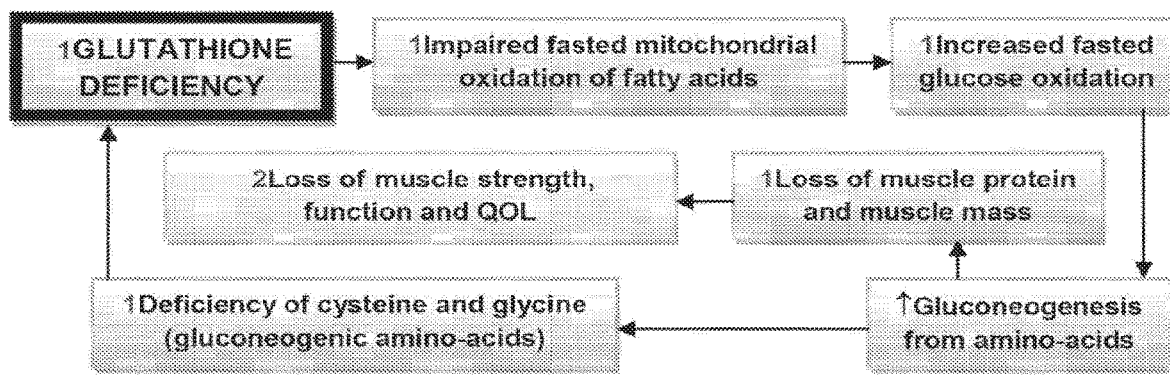
FIG. 1 illustrates exemplary relationships between glutathione deficiency and certain physical states.

As used herein the specification, "a" or "an" may mean one or more. As used herein in the claim(s), when used in conjunction with the word "comprising", the words "a" or "an" may mean one or more than one. As used herein "another" may mean at least a second or more.

As used herein, the term "complications from diabetes" in specific embodiments refers to diabetic nephropathy, neuropathy, retinopathy, diabetic obesity, diabetic dyslipidemia, cardiometabolic syndrome, and combinations thereof, for example.

As used herein, the term "effective amount" refers to an amount of glycine and n-acetylcysteine (or functional derivatives thereof) that is required to improve at least one symptom of a medical condition in an individual; in specific embodiments, the medical condition exists in the individual directly or indirectly because of insufficient levels of glutathione. In specific embodiments, the effective amount refers to the amount of glycine and n-acetylcysteine that is utilized to increase glutathione levels in the individual.

As used herein, the term "elderly" refers to an individual over the age of at least 60 years of age.

As used herein, the term "oxidative stress" refers to the state in an individual, or cell or tissue of an individual, of an imbalance between the production of reactive oxygen and the ability to detoxify the reactive intermediates or easily repair the resulting damage in a biological system. The natural reducing environment within cells is maintained by processes using a constant input of metabolic energy, and disturbances in this normal redox state can result in toxic effects through the production of, for example, free radicals and peroxides that damage cellular components, such as proteins, lipids, and/or DNA, for example.

II. General Embodiments

Embodiments of the disclosure include methods of increasing blood levels of cysteine and glycine (e.g., cysteinylglycine) to increase intracellular GSH, cysteine, and/or glycine and/or to reduce CRP levels. In some embodiments, mechanisms of action involve cysteine and/or glycine but are independent of GSH.

In certain embodiments of the invention, there are methods and compositions for the treatment of medical conditions caused directly or indirectly by insufficient GSH levels in the individual. The individual may be of any age or state of health, although in particular embodiments the individual is elderly, is susceptible to particular medical conditions or physical states associated directly or indirectly with insufficient GSH levels, or has a medical condition or physical state that is associated directly or indirectly with insufficient GSH levels. The compositions delivered to the individual in such cases include at least glycine and n-acetylcysteine, in particular as precursor amino acids to facilitate raising glutathione levels in the individual. One can measure red blood cell GSH, or a muscle biopsy to measure GSH levels intracellularly, for example. Intracellular GSH measuring assays are known in the art (Rahman et al., 2007).

In specific embodiments, one or more medical conditions that are caused directly or indirectly by reduced levels of cysteine, glycine, and/or GSH are treated or prevented with effective amounts of glycine or a functional derivative thereof and N-acetylcysteine or a functional derivative thereof. In particular embodiments, the medical condition or physical state is one or more of the following: (a) muscle loss; (b) deleterious effects of weightlessness; (c) organ damage; (d) cardiac function or failure; (e) cancer prevention; (f) fetal metabolic programming for prevention of later development of obesity and/or diabetes; (g) maternal and fetal health in gestational diabetes; (h) exercise capacity and physical function; (i) obesity; (j) longevity; (k) hepatotoxicity; (l) neurodegenerative disease; (m) prophylaxis for nephropathy; (n); prevention for acetaminophen toxicity; (o) non-alcoholic steatohepatitis; (p) alcohol hangover; (q) hearing impairment; (r) Alzheimer's Disease; (s) Parkinson's Disease; (t) osteoporosis, (u) hypertension; (v) polycystic ovary syndrome (PCOS); (w) atherosclerosis; (x) coronary artery disease; (y) myocardial damage after stress; (z) insufficient immunity following vaccination; (aa) cystic fibrosis; (bb) traumatic brain injury; (cc) concussion; (cc) concussion; (dd) ototoxicity; (ee) tinnitus; (ff) vertigo; (gg) dizziness; (hh) Meniere's Disease; (ii) post-traumatic recovery and survival (e.g., post-surgical, post-sepsis, post-blunt or penetrating trauma due to accident or physical assault, etc.); (jj) non-alcoholic fatty liver disease (NAFLD) and (kk) a combination thereof. The individual may be diagnosed with such condition(s) or may be suspected of having such condition(s) or may be susceptible to such condition(s). The individual may be treated with other therapy or therapies in addition to methods of the disclosure.

In specific embodiments, an individual is provided effective amounts of compositions as described herein for the explicit purpose of raising intracellular levels of GSH, cysteine, and/or glycine and because it is determined that the individual is afflicted with a condition for which such levels are directly or indirectly related. In specific cases, methods of the disclosure include the diagnosis of such medical condition(s).

III. Pharmaceutical Compositions

In particular embodiments, the present invention is directed to pharmaceutical compositions for use in treating, preventing, or delaying the onset of a medical condition or physical state that is directly or indirectly related to reduced intracellular GSH levels. In specific embodiments, the compositions consist of, consisting essentially of, or comprise glycine (or a functional derivative thereof) and N-acetylcysteine (or a functional derivative thereof). A functional derivative of glycine is defined as a glycine derivative that is effective in an individual in by itself or in conjunction with N-acetylcysteine (or a functional derivative thereof) to increase intracellular GSH levels. A functional derivative of N-acetylcysteine is defined as a N-acetylcysteine derivative that is effective in an individual in by itself or in conjunction with glycine (or a functional derivative thereof) to increase intracellular GSH levels. In specific embodiments, a "cysteine" derivative, i.e., a functional derivative of cysteine that is effective in an individual in by itself or in conjunction with glycine, may be employed.

The glycine component and N-acetylcysteine component may be provided together or separately. In specific embodiments, the composition comprises N-acetylcysteinylglycine; cysteinylglycine and all its forms, e.g., L-cysteinylglycine; and so forth. Examples of glycine derivatives includes at least D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)—N-Boc-(2'-chlorophenyl)glycine; Boc-L-cyclopropylglycine; Boc-L-cyclopropylglycine; (R)—N-Boc-4-fluorophenylglycine; Boc-D-propargylglycine; Boc-(S)-3-thienylglycine; Boc-(R)-3-thienylglycine; D-α-Cyclohexylglycine; L-α-Cyclopropylglycine; N-(2-fluorophenyl)-N-(methylsulfonyl) glycine; N-(4-fluorophenyl)-N-(methylsulfonyl)glycine; Fmoc-N-(2,4-dimethoxybenzyl)-Gly-OH; N-(2-Furoyl)glycine; L-α-Neopentylglycine; D-Propargylglycine; sarcosine; Z-α-Phosphonoglycine trimethyl ester; and so forth.

In particular embodiments, the pharmaceutical compositions comprise N-acetylcysteine (NAC), L-glycine, L-glycine ethyl ester, and/or dipeptide forms, e.g., cysteinylglycine.

In specific embodiments, glycine is administered at 1.33 mmol/kg/d and NAC is administered at 0.83 mmol/kg/d for a particular period of time. Durations of treatment may last for one or more days, 1 week, 2 weeks, 3 weeks, one month, two months, three months, four months, five months, six months, one year, two years, five years, ten years, fifteen years, twenty years, twenty-five years, thirty years, and so forth, for example. In some cases the treatment lasts for the remaining life of the individual. In specific embodiments, the administration occurs until no detectable symptoms of the medical condition remain. In specific embodiments, the administration occurs until a detectable improvement of at least one symptom occurs and, in further cases, continues to remain ameliorated.

Where the invention is directed to treating with the compounds of the present invention, administration of the compounds of the invention with a suitable pharmaceutical excipient as necessary can be carried out via any of the accepted modes of administration. The compounds may be comprised in a pharmaceutically acceptable excipient, which may be considered as a molecular entity and/or composition that does not produce an adverse, allergic and/or other untoward reaction when administered to an animal, as appropriate. It includes any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated.

Thus, administration can be, for example, intravenous, topical, subcutaneous, transcutaneous, intramuscular, oral, intra-joint, parenteral, peritoneal, intranasal, intravesical or by inhalation. Suitable sites of administration thus include, but are not limited to, skin, bronchial, gastrointestinal, anal, vaginal, eye, bladder, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, aerosols or the like, preferably in unit dosage forms suitable for simple administration of precise dosages.

The compositions typically include a conventional pharmaceutical carrier or excipient and may additionally include other medicinal agents, carriers, adjuvants, and the like. Preferably, the composition will be about 5% to 75% by weight of a compound or compounds of the invention, with the remainder consisting of suitable pharmaceutical excipients. Appropriate excipients can be tailored to the particular composition and route of administration by methods well known in the art, e.g., REMINGTON'S PHARMACEUTICAL SCIENCES, 18TH ED., Mack Publishing Co., Easton, Pa. (1990).

For oral administration, such excipients include pharmaceutical grades of mannitol, lactose, starch, magnesium stearate, sodium saccharine, talcum, cellulose, glucose, gelatin, sucrose, magnesium carbonate, and the like. The composition may take the form of a solution, suspension, tablet, pill, capsule, powder, sustained-release formulation, and the like.

In some embodiments, the pharmaceutical compositions take the form of a pill, tablet or capsule, and thus, the composition can contain, along with the biologically active conjugate, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof.

The active compounds of the formulas may be formulated into a suppository comprising, for example, about 0.5% to about 50% of a compound of the invention, disposed in a polyethylene glycol (PEG) carrier (e.g., PEG 1000 [96%] and PEG 4000 [4%]).

Liquid compositions can be prepared by dissolving or dispersing compound (about 0.5% to about 20%), and optional pharmaceutical adjuvants in a carrier, such as, for example, aqueous saline (e.g., 0.9% w/v sodium chloride), aqueous dextrose, glycerol, ethanol and the like, to form a solution or suspension, e.g., for intravenous administration. The active compounds may also be formulated into a retention enema.

If desired, the composition to be administered may also contain minor amounts of non-toxic auxiliary substances such as wetting or emulsifying agents, pH buffering agents, such as, for example, sodium acetate, sorbitan monolaurate, or triethanolamine oleate.

For topical administration, the composition is administered in any suitable format, such as a lotion or a transdermal patch. For delivery by inhalation, the composition can be delivered as a dry powder (e.g., Inhale Therapeutics) or in liquid form via a nebulizer.

Methods for preparing such dosage forms are known or will be apparent to those skilled in the art; for example, see Remington's Pharmaceutical Sciences, supra., and similar publications. The composition to be administered will, in any event, contain a quantity of the pro-drug and/or active compound(s) in a pharmaceutically effective amount for relief of the condition being treated when administered in accordance with the teachings of this invention.

Generally, the compounds of the invention are administered in a therapeutically effective amount, i.e., a dosage sufficient to effect treatment, which will vary depending on the individual and condition being treated. Typically, a therapeutically effective daily dose is from 0.1 to 100 mg/kg of body weight per day of drug. Most conditions respond to administration of a total dosage of between about 1 and about 30 mg/kg of body weight per day, or between about 70 mg and 2100 mg per day for a 70 kg person.

Stability of the conjugate can be further controlled by chemical alterations, including D amino acid residues in the polypeptide chain as well as other peptidomimetic moieties. Furthermore, stability of the conjugates could also be enhanced by unnatural carbohydrate residues.

The glycine and N-acetylcysteine components may be formulated in a particular ratio. In certain embodiments, the formulation may comprise the components in the following exemplary ratios: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, 1:150, 1:200, 1:300, 1:400, 1:500, 1:600, 1:750, 1:1000, 1:10,000, and so forth, for example. In particular embodiments, the formulation may comprise the components in the following percentages by formulation (either the same or different percentages for each): 1%, 2%, 3%, 4%, 5%, 6%, 7%, 8%, 9%, 10%, 12%, 15%, 20%, 25%, 30%, 40%, 45%, 50%, 55%, 60%, 65%, 70%, 75%, 80%, 85%, 90%, 95%, 97%, or 99%, for example.

Glycine (or a functional derivative) and N-acetylcysteine (or a functional derivative) may be delivered in the same composition or in different compositions. In embodiments wherein glycine (or a functional derivative) and N-acetylcysteine (or a functional derivative) are provided separately, the regimen for their separate delivery may be of any suitable kind. In specific embodiments, the glycine is provided to the individual prior to the N-acetylcysteine, at the same time as N-acetylcysteine, or subsequent to N-acetylcysteine. Separate deliveries may encompass the same route of administration but at different times or may be different routes of administration.

IV. Combination Treatments

Alternatively, the treatment of the invention may precede, follow, or both another treatment by intervals ranging from minutes to weeks. In embodiments where the inventive composition(s) and the other agent are provided separately to an individual, one would generally ensure that a significant period of time did not expire between the time of each delivery, such that the inventive composition and the other agent would still be able to exert an advantageously combined effect on the cell. In such instances, it is contemplated that one may deliver both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, for example, wherein the inventive treatment is "A" and the secondary agent for the medical condition of the invention as described herein, such as diabetic treatment (for example only), is "B":

| |
|---|
| A/B/A B/A/B B/B/A A/A/B A/B/B B/A/A A/B/B/B B/A/B/B |
| B/B/B/A B/B/A/B A/A/B/B A/B/A/B A/B/B/A B/B/A/A |
| B/A/B/A B/A/A/B A/A/A/B B/A/A/A A/B/A/A A/A/B/A |

Administration of the inventive compositions of the present invention to a patient will follow general protocols for the administration of drugs, taking into account the toxicity, if any, of the molecule. It is expected that the treatment cycles would be repeated as necessary. It also is contemplated that various standard therapies, as well as surgical intervention, may be applied in combination with the described therapy.

V. Kits

Therapeutic kits associated with the compositions of the present invention comprise another aspect of the present invention. Such kits will generally contain, in suitable container means, an inventive composition of the present invention. The kit may have a single container means that contains the inventive composition or it may have distinct container means for the inventive composition and other reagents that may be included within such kits.

The components of the kit may be provided as liquid solution(s), or as dried powder(s). When the components are provided in a liquid solution, the liquid solution is an aqueous or non-aqueous solution, with a sterile aqueous or non-aqueous solution being particularly preferred. When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the composition may be placed, and preferably suitably aliquoted. Where a second agent is provided, the kit will also generally contain a second vial or other container into which this agent may be placed. The kits of the present invention will also typically include a means for containing the agent containers in close confinement for commercial sale. Such containers may include injection or blow-molded plastic containers into which the desired vials are retained, for example.

In the kit of the invention, the glycine (or functional derivative thereof) and the N-acetylcysteine (or functional derivative thereof) may be provided separately or in a mixture together.

VI. Examples

The following examples are included to demonstrate preferred embodiments of the invention. It should be appreciated by those of skill in the art that the techniques disclosed in the examples which follow present techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Metabolic Basis of Sarcopenic-Obesity in Aging: Role of Glutathione

Elderly humans have the highest risk of becoming overweight or developing obesity. Together with the decreased prevalence of muscle mass in this population, elderly humans develop a phenotype of 'sarcopenic-obesity', with decreased muscular strength and lower quality of life, but underlying mechanisms are not well understood and effective therapy is lacking. Translational work in humans and rodents has led to the discovery that deficiency of the most abundant endogenous antioxidant glutathione (GSH) in aging is linked to mitochondrial dysfunction, and in some embodiments, this provides a mechanistic explanation for the development of sarcopenic-obesity in elderly humans. GSH deficiency in elderly humans is caused by diminished synthesis, due to limited availability of its precursor amino-acids cysteine and glycine. Short-term supplementation of these amino acids is sufficient to correct their own deficiency, and to also restore the intracellular synthesis and concentrations of GSH. Compared to fasted healthy young human controls, fasted GSH-deficient elderly humans had severe impairment of mitochondrial fatty-acid oxidation (which could promote fat storage), together with increased carbohydrate oxidation (which could contribute to muscle loss). Since mitochondrial fuel preference in the fasted state is fatty-acids and not glucose, this abnormal reversal in fasted fuel preference suggests impaired mitochondrial energetics. Interestingly, the restoration of GSH synthesis in these elderly humans over 2-weeks with cysteine and glycine precursor supplementation led to complete restoration of fasted mitochondrial fatty acid and carbohydrate oxidation to levels seen in young controls. Based on these data it was considered that impaired mitochondrial fatty-acid oxidation forces a shift in fuel oxidation to glucose to meet energy needs. Since in the fasted state glucose is provided by gluconeogenesis of which muscle protein is a significant contributor, this would result in loss of muscle protein (and thus muscle mass), as well as deficiency of cysteine and glycine (known gluconeogenic amino acids) to further propagate GSH deficiency. Loss of muscle mass in turn would lead to diminished muscle strength. Supplementing cysteine and glycine could correct GSH deficiency and break this negative spiral to correct mitochondrial fatty acid oxidation (and thus lower total body fat), reduce carbohydrate oxidation (and thus spare muscle protein loss to increase lean mass) and increase muscle strength. Support for this consideration comes from a study in HIV patients with biological aging where improvement of GSH deficiency with cysteine and glycine supplementation (used at the same doses and duration as the elderly studies) was associated with restoration of fasted mitochondrial fuel oxidation, 3.5 lb decrease in total body fat mass, 1.9 lb increase in lean mass and significant increases in muscle strength in the dominant and non-dominant arms within a 2-week timeframe.

Example 2

Preventing and Treating Sarcopenia, Sarcopenic Obesity, Cachexia and Muscle Wasting Sarcopenia is the degenerative loss of skeletal muscle mass, quality, and strength associated with aging. Sarcopenia can also be secondary to disuse and zero gravity or weightlessness. Cachexia is a complex metabolic wasting syndrome characterized by loss of weight, muscle atrophy weakness and fatigue which accompanies a range of chronic illnesses including cancer, HIVAIDS, COPD, degenerative neurologic disorders such as multiple sclerosis, congestive heart disease, tuberculosis and renal disease. Sarcopenia can be associated with an increase in fat mass, i.e., sarcopenic obesity, and cachexia can be associated with or without loss of fat mass.

These conditions represent principle targets for prevention and treatment by providing cysteine plus glycine to raise intracellular GSH and improve muscle health in mammals. Improvement of GSH by administering its precursors cysteine and glycine is associated with an improved physiological pattern of mitochondrial fuel oxidation, lower total body fat, waist circumference and insulin resistance, and higher fat-free mass and muscle strength in older HIV-infected patients suggesting that this method can prevent and reverse sarcopenia, sarcopenic obesity, and cachexia.

Example 3

Prevention and Treatment for Drug and Other Toxicities

A variety of drugs induce mitochondrial toxicity and/or hepatotoxicity, including, for example, acetaminophen and anti-retrovirals. Certain drugs that cause mitochondrial toxicity include at least anticonvulsants, psychotropics (antidepressants, antipsychotics, barbiturates, and anxiety medications), cholesterol medications, analgesics/anti-inflammatory drugs, antibiotics, anti-arrhythmics, steroids, anti-viral medications, anti-retroviral medications, cancer medications, diabetes medications, beta-blockers, and immunizations. Specific drugs include valproate, amitriptyline, amoxapine, fluoxetine, citalopram, chlorpromazine, fluphenazine, haloperidol, resperidone, phenobarbital, secobarbital, butalbital, amobarbital, pentobarbital, alprazolam, diazepam, statins, bile acids-cholestyramine, ciprofibrate, fenofibrate, aspirin, acetaminophen, indomethacin, naproxen, diclofenac, tetracycline, minocycline, chloramphenicol, tenofovir, darunavir, ribavirin, telaprevir, aminoglycosides, linezolid, amiodarone, interferon, zidovudine, doxorubicine, cis-platinum, tamoxifen, and metformin.

In particular embodiments, NAC and/or glycine are provided to an individual to prevent, treat, or reduce the deleterious effects of mitochondrial toxicity and/or hepatotoxicity. In specific embodiments, other toxicities related to oxidative stress and/or GSH deficiency are treated with methods of the present disclosure.

In specific embodiments, there are methods for the prevention and treatment for acetaminophen toxicity, such as in the context of hepatotoxicity. Hepatotoxicity is a serious problem during drug development and for the use of many established drugs. For example, acetaminophen overdose is currently the most frequent cause of acute liver failure in the United States. Hepatic mitochondria are critical targets for drug toxicity, either directly or indirectly through the formation of reactive metabolites. Acetaminophen (Tylenol®, paracetamol, N-acetyl-p-aminophenol; APAP) is a widely used over-the-counter analgesic and antipyretic drug. It is also often combined with hydrocodone, propoxyphene, codeine, and oxycodone in a number of prescription narcotic drugs. At therapeutic doses, acetaminophen has analgesic and antipyretic effects similar to those of aspirin and ibuprofen but it has a very narrow therapeutic window Acetaminophen is a leading cause of acute liver failure, even at doses that are within the recommended range. It accounts for tens of thousands of calls to poison control centers and hospital admissions each year, as well as hundreds of deaths. Both alcohol consumption and fasting (due to illness, anorexia, or malnutrition) greatly increase the risk of liver injury due to acetaminophen.

Conditions such as advanced age, alcohol consumption, and fasting (due to illness, anorexia, or malnutrition, for example), and even the metabolite of acetaminophen itself greatly increase the risk of liver injury by decreasing levels of glutathione, an antioxidant that helps the liver detoxify acetaminophen. Even at standard doses, the metabolism of acetaminophen in humans releases small amounts of a toxic substance, N-acetyl-benzoquinoneimine (or NAPQI). With excessive doses, much larger amount of this toxin is formed. There is a fine line between a safe dose of acetaminophen and one that is dangerous, which means that doses even slightly above the maximum recommended dose of 4 g/day can cause liver damage.

Utilizing optimal intracellular glutathione concentrations in the liver is a logical preventative and treatment approach to acetaminophen toxicity. N-acetylcysteine administration has been used as a primary treatment for the liver toxicity triggered by acetaminophen overdose through its ability to maintain hepatic glutathione stores. In specific embodiments, raising hepatic GSH levels with NAC/Glycine before, with, and/or following acetaminophen mitigates the toxic effects of acetaminophen, even at prescribed levels.

Example 4

Improvement of Physical Performance

Methods and/or compositions of the disclosure may be provided to individuals for the improvement of physical performance, prevention of loss of muscle mass by enhancing the effect of exercise, recovering from intense exercise, or reversing loss of lean muscle mass caused by non-disease conditions that accelerate aging and muscle loss in otherwise young, physically fit individuals, such as astronauts (zero gravity), marathon runners, firefighters, elite athletes, and so forth. Also, endurance activities especially increase oxidative stress, which can be particularly of concern in older athletes who may already have deficiency in intracellular GSH. Therefore, in specific embodiments methods of the disclosure prevent and/or treat the oxidative stress of exercise.

Example 5

Longevity

Figure 6:
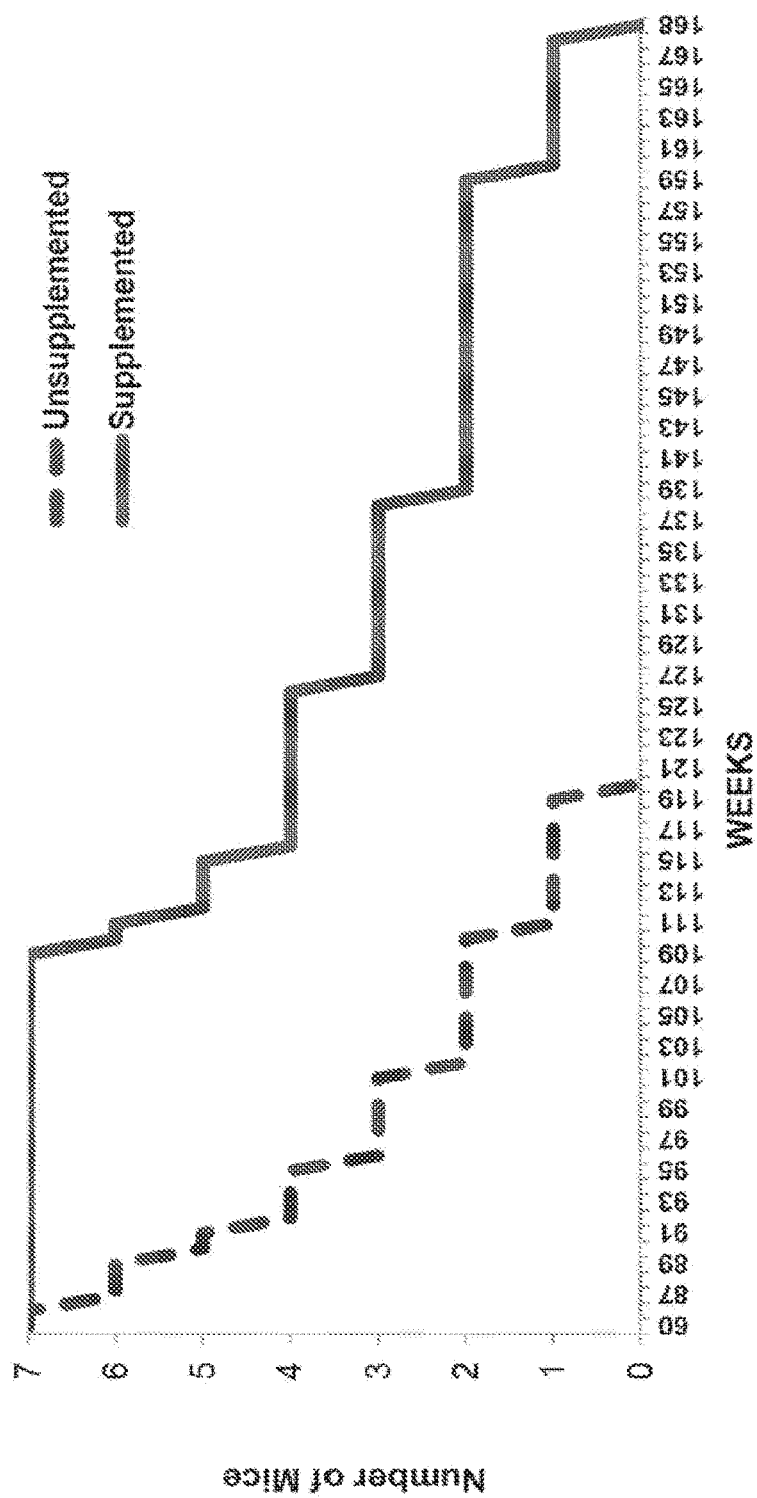
FIG. 6 shows the lifespan of mice receiving N-acetylcysteine and glycine.

Supplementing feed of aged mice with cysteine (as n-acetylcysteine) and glycine is sufficient to boost levels of the antioxidant glutathione. Glutathione restoration in these aged mice led to significant improvement in mitochondrial fuel oxidation. Because these beneficial changes are useful to impact length of life, it was tested whether supplementing cysteine (as n-acetylcysteine) and glycine in the feed of mice extends their lifespan. The study was conducted as follows: 60-week old mice were studied in 2 groups (7 mice, with 2 females and 5 males in each group), and both groups were matched for sex, age and weight. One group was allowed to eat a regular feed ad libitum, and the second group was fed a diet containing additional cysteine (as n-acetylcysteine) and glycine. However the feed content of both diets were matched such that they had identical amount of calories and protein nitrogen per gram of feed, i.e. both diets were isocaloric and isonitrogenous. Monitoring of feed weights showed that feed consumption was similar in both groups. The animals were allowed free access to their respective diets and water and length of life was noted as the primary outcome measure. The results showed that the mice receiving the cysteine and glycine supplemented diet lived 34 weeks longer on average, which represents a 35% increase in lifespan (FIG. 6).

Example 6

HIV in the Elderly

Patients infected with HIV and aged over 50 years are reported to have accelerated functional decline with lower muscle mass, decreased muscular strength and functional limitations comparable to geriatric non-HIV patients, but underlying mechanisms for these defects are not well understood and effective therapy is lacking. Recognizing this, the Centers for Disease Control has suggested that the cutoff for being 'old' in HIV patients begins at 50 years.

In specific embodiments of the disclosure, functional decline in older HIV-infected patients is linked to impaired mitochondrial function. Mitochondria depend on antioxidants for defense against damaging reactive oxygen species and oxidative stress. Glutathione (GSH), the most abundant endogenous intracellular antioxidant and a key component of mitochondrial antioxidant defenses, is known to be deficient in HIV patients. For mechanisms contributing to GSH deficiency in older HIV patients, this occurs because of severely diminished GSH synthesis caused by deficiency of two of its precursor amino acids: cysteine and glycine. Two-weeks of oral dietary supplementation with cysteine and glycine corrected deficiency of these amino acids, increased GSH synthesis, improved intracellular GSH concentrations, and lowered ROS levels and oxidative damage. Under physiological conditions, the fuel of choice in the fasted state is fatty acids (FA), and not glucose. GSH-deficient older HIV patients had severely impaired fasted FA oxidation and higher fasted glucose oxidation, suggesting a mitochondrial defect. Improvement in GSH concentrations led to a striking increase in increased fasted mitochondrial FA oxidation and decrease in glucose oxidation. These changes were associated with a significant increase in fat-free mass and muscle strength. Interestingly, the muscle strength of these patients increased significantly when GSH levels increased—while their muscle strength in the GSH-deficient state was equivalent to that of 80-year old non-HIV humans, with an increase in GSH their muscle strength increased to that of 70-year old humans. Effectively, these older HIV patients became 10 years 'younger' in a 2-week timeframe with improvement of GSH.

One can investigate whether GSH deficiency contributes to loss of muscle mass, strength, functional limitations and quality of life in older-HIV patients, and test whether supplementation with cysteine and glycine to correct GSH deficiency will reverse these defects. One can perform an open-label study in 10 older-HIV patients and 10 non-HIV controls (matched for age, gender and BMI) aged 50-60 y, for example. Based on published data, a sample size of 8 subjects are needed and one can study 10 subjects to account for 20% attrition. All subjects can be studied at baseline, and only the HIV subjects may be studied again after receiving cysteine plus glycine for 12-weeks. One can test whether compared to non-HIV controls, GSH deficiency in older HIV patients correlates with impaired fasted mitochondrial fuel oxidation and muscle protein loss, and whether supplementation with cysteine plus glycine can reverse these defects.

In specific embodiments for older HIV patients, GSH deficiency leads to defective fasted mitochondrial fuel oxidation, elevated glucose oxidation and muscle protein loss, and that GSH restoration can reverse these defects. Although not to be limited by theory, GSH deficiency results in impaired fasted mitochondrial NEFA oxidation, forcing a shift to glucose oxidation for energy needs. Because glucose in the fasted state is provided by gluconeogenesis mainly from muscle protein, this leads to muscle loss, and cysteine and glycine deficiency (FIG. 1). Supplementing cysteine plus glycine to correct GSH deficiency will restore fasted mitochondrial FA oxidation and lower glucose oxidation, thus decreasing muscle protein loss toward gluconeogenesis, and thereby increase muscle mass. For such considerations, one can measure muscle GSH, cysteine and glycine levels (HPLC), fasted NEFA and glucose oxidation (calorimetry), muscle protein loss (stable isotope studies), muscle mass (DEXA, total body potassium and nitrogen scans).

One can test whether, compared to non-HIV controls, GSH deficiency in older HIV patients is correlated to decreased muscle mass, muscle strength and function, and if GSH restoration will restore muscle strength, and function to matched non-HIV controls. In specific embodiments, GSH deficiency in older HIV patients underlies loss of muscle strength and function, and GSH restoration can improve strength and function that in a matched non-HIV group. In such consideration, one can measure strength (such as with forearm grip by dynamometry) and function (such as with a 6-minute walk).

Older HIV patients have impaired mitochondrial oxidation and muscle protein loss, but underlying mechanisms are unknown. Because >50% of HIV patients are expected to be older (>50 y of age) by 2015, complications from these defects will significantly increase human burden and health care costs. The present disclosure provides for prevention and reversal of muscle loss, increased muscle strength, improved function and quality of life in older HIV patients, and lower healthcare costs in an increasing population of older HIV patients. In specific embodiments, GSH deficiency is a novel and vital risk factor for muscle loss in older HIV patients, and one can provide therapy based on cysteine plus glycine supplementation to correct GSH deficiency and reverse muscle loss. In specific embodiments, one can increase muscle mass and strength, exercise capacity, and improve quality of life. Embodiments of the disclosure provide a novel, simple, safe, effective and inexpensive nutritional strategy to correct GSH deficiency in older HIV patients with cysteine plus glycine.

In specific embodiments, in older patients with HIV, GSH deficiency underlies impaired fasted mitochondrial fuel oxidation, loss of muscle mass, strength and function and contributes to accelerated functional decline. One can use innovative stable-isotope tracer-based protocols, calorimetry, DXA, total body potassium and nitrogen scans, dynamometry, and functional testing to measure outcomes at the level of whole-body (NEFA and glucose oxidation and muscle loss), and tissue (muscle GSH and protein loss). One shows that benefits occur because of cysteine and glycine supplementation. Embodiments of the disclosure provide a novel, simple, safe, effective and inexpensive nutritional strategy using cysteine plus glycine to correct defects in mitochondrial fuel oxidation, loss of muscle protein, muscle mass and strength, and quality of life in older HIV patients.

HIV and GSH deficiency: RBC-GSH levels were measured in young (age 30-40 y; n=10) and old (age 50-60 y; n=20) HIV patients and low GSH was found in all patients, but age was significantly associated with even lower GSH concentrations (P<0.0001). Further analysis showed that 55-year old HIV patients had GSH levels comparable to 70-year old non-HIV humans.

Figure 2:
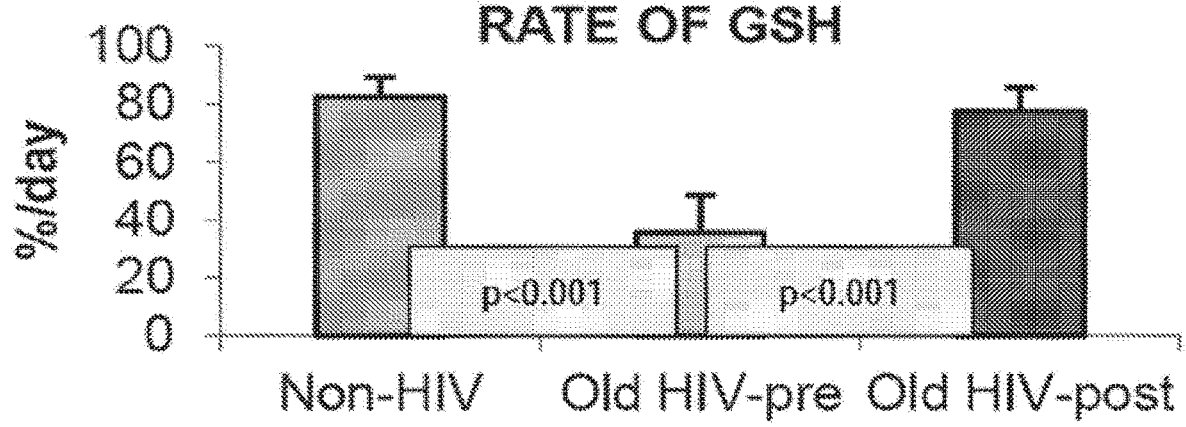
FIG. 2 shows a fractional synthesis rate of GSH in older HIV patients compared to controls.
Figure 3:
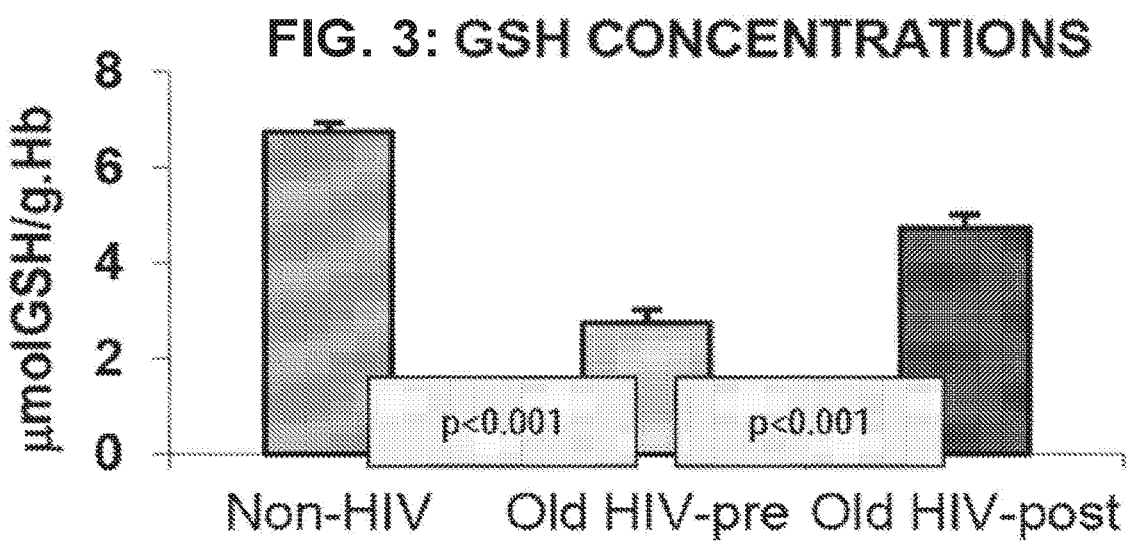
FIG. 3 demonstrates GSH concentrations in older HIV patients compared to controls.

GSH kinetics in older HIV patients (FIGS. 2,3): GSH kinetics were studied in 8 older GSH-deficient HIV patients (~55 y) before and after supplementation with cysteine plus glycine as GSH precursors. Results compared to historical GSH-replete non-HIV controls (n=8) showed severe intracellular deficiency of cysteine and glycine in older HIV patients that improved with supplementation. As shown, pre-supplemented HIV subjects had 58% lower GSH-FSR and 57% lower GSH levels (compared to controls). Post-supplementation, GSH-FSR (where FSR is fractional synthetic rate) and GSH levels increased by 120% and 53% respectively.

Figure 4:
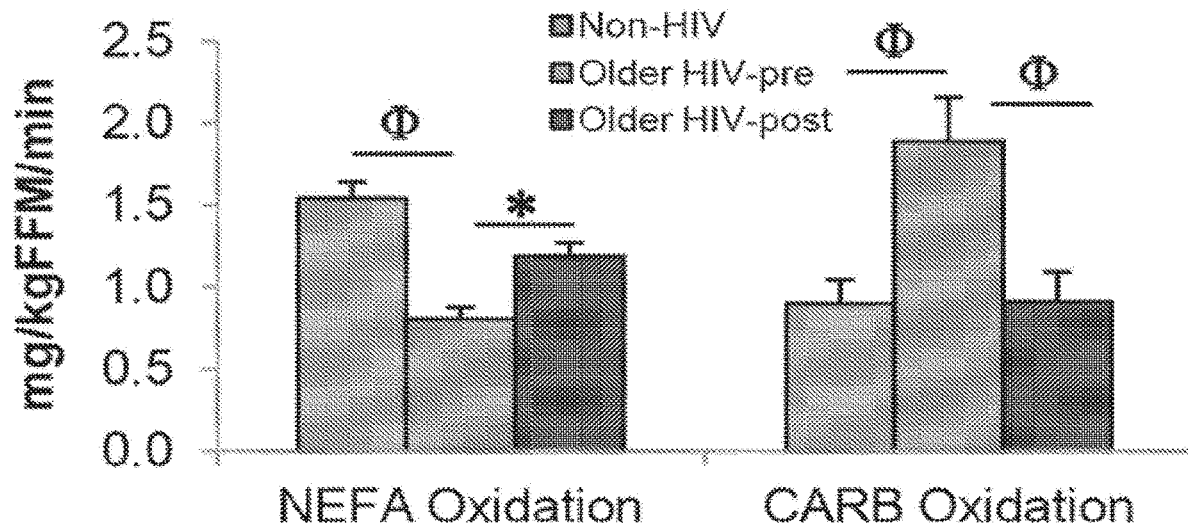
FIG. 4 shows fasted fuel oxidation in older HIV patients compared to controls.

Fasted fuel oxidation in older HIV subjects (FIG. 4): After a 16-hour fast, GSH-deficient older HIV subjects had significantly lower NEFA oxidation and higher carbohydrate (CARB) oxidation compared to non-HIV controls. Restoring GSH synthesis led to 46% increase in NEFA oxidation, and 49% fall in carbohydrate oxidation. (*=p<0.05; Φ=p<0.01).

GSH improvement increases fat-free mass and strength: GSH improvement led to a significant 0.9 kg increase in fat-free mass (p=0.003), and muscle strength in both forearms (p<0.01).

Thus, older HIV patients have GSH deficiency because of diminished synthesis (caused by decreased availability of its precursors cysteine and glycine), and it is associated with impaired mitochondrial fuel oxidation, loss of muscle mass and strength. Cysteine and glycine supplementation for 2 weeks increases GSH levels. Longer 12-week duration of supplementation restores GSH concentrations fully, and reverses muscle loss and functional decline in older HIV patients, in specific embodiments.

Example 7

C-Reactive Protein

C-reactive protein (CRP) is an acute-phase protein found in the blood plasma, and is synthesized by the liver. Levels of CRP rise in response to inflammation, and therefore it is considered a biomarker for conditions associated with increased inflammation. CRP has also been identified as a biomarker for cardiovascular disease—levels >3 µg/ml are considered undesirable, and levels <1 µg/ml are optimal. Elevated CRP has also been linked to diabetes, HIV and aging. There are limited interventions to lower CRP levels. Powerful cholesterol lowering medications in the class of agents known as statins can lower CRP levels.

Figure 5:
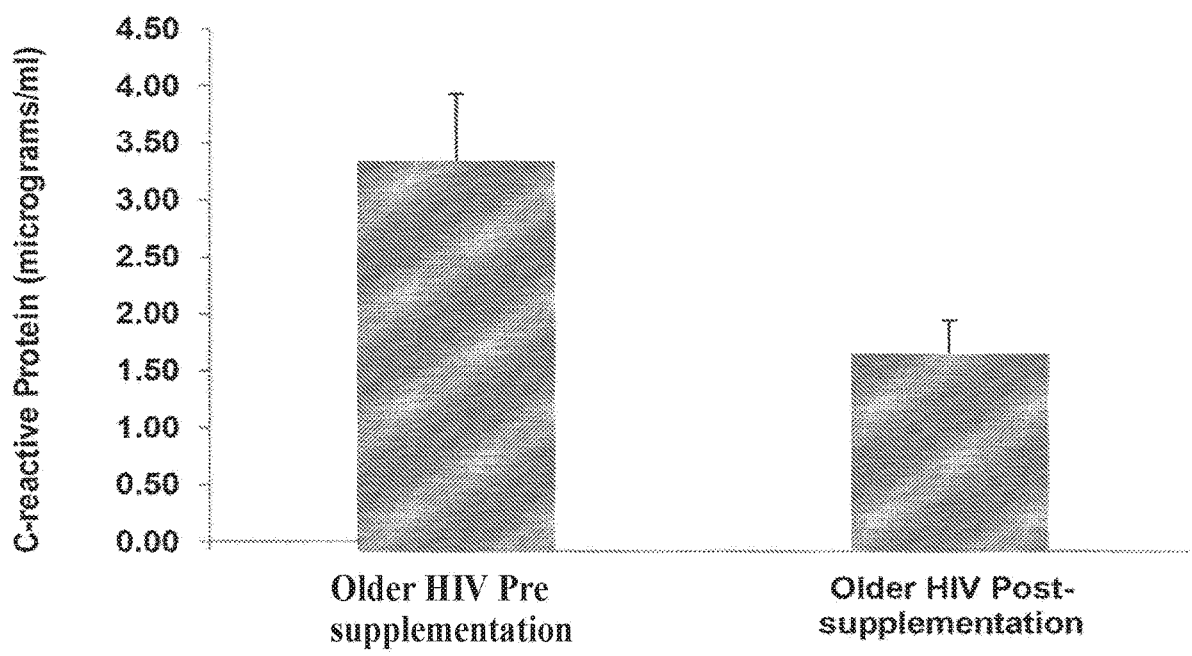
FIG. 5 demonstrates C-reactive protein levels in older HIV patients before and after supplementation with oral supplementation of N-acetylcysteine and glycine.

Older HIV patients with glutathione deficiency had high levels of CRP, and this fell significantly (p<0.05) when glutathione levels were increased using oral dietary supplementation of cysteine (as n-acetylcysteine) and glycine (FIG. 5).

Example 8

Improvement of Mitochondrial Defect Following Drug Intake

Certain drugs cause toxicity because their mechanism of action results in mitochondrial dysfunction or impairment. In certain embodiments, there are methods of neutralizing or mitigating drug-induced mitochondrial dysfunction or impairment by providing to the individual an effective amount of a composition comprising glycine or a functional derivative thereof and N-acetylcysteine or a functional derivative thereof. The toxicity caused by the drug may be of any kind that causes mitochondrial dysfunction or impairment, but in specific embodiments the drug is an antiviral drug, such as an HIV drug, hepatitis drug, and so forth. Drug toxicity could also be caused or exacerbated by depletion in GSH either prior to or post-treatment, in certain embodiments.

Drugs that cause mitochondrial toxicity include at least anticonvulsants; psychotropics (Antidepressants; Antipsychotics; Barbiturates; Anxiety medications); Cholesterol medications; Analgesic/anti-inflammatory drugs; Antibiotics; Anti-arrhythmic drugs; Steroids; Anti-viral drugs; Anti-retroviral drugs; Cancer medications; Diabetes medications; Beta-blockers; and immunizations.

In specific cases, the drug is Valproate (Depakote); Amitriptyline (Elavil); Amoxapine; Fluoxetine (Prozac); Citalopram (Cipramil); Clorpromazine (Thorazine); Fluphenazine (Prolixin); Haloperidol (Haldol); Resperidone (Risperdol); Phenobarbital; Secobarbital (Seconal); Butalbital (Fiornal); Ambarbital (Amytal); Pentobarbital (Nembutal); Alprazolam (Xanax); Diazepham (Valium, Diastat); Statins; Bile acids-cholestryamine; Ciprofibrate; ASA (Aspirin); Acetaminophen (Tylenol); Indomethacin (Indocin); Naproxen (Aleve); Diclofenac; Tetracycline, minoclycline; Chloramphenical; Aminoglycosides; Linozolid (Zyvox); Amiodarone; Interferon; Zidovudine; Doxorubicine (Adriamycin); Cis-platinum; Tamoxifen; Metformin; cystuc; or a mixture thereof.

In such situations wherein an individual is in need of taking a medication that is known or suspected of having drug toxicity because of mitochondrial impairment or reduction in GSH, the individual may also be provided a composition that comprises glycine or a functional derivative thereof and N-acetylcysteine or a functional derivative thereof. In specific cases, the drug having mitochondrial toxicity is given to an individual at the same time and/or before and/or after the glycine or a functional derivative thereof and N-acetylcysteine or a functional derivative thereof is given to the individual.

Example 9

Physiological Benefit to Increasing GSH Concentration

1. HIV and TNF alpha: 8 patients with HIV had plasma measurement of TNF-alpha concentrations before and 2-weeks after supplementation of cysteine and glycine to increase GSH concentrations. The data showed that TNF-alpha decreased from 34.6±7.5 to 27.8±4.7 (p=0.00049).

2. Neurocognitive data: 3 HIV patients had measurement of neurocognitive assessments before and after 12 weeks of supplementation with cysteine and glycine to increase GSH concentrations. The data showed an improvement in neurocognitive function as shown below:
   Trail making test (composite index) 38±3 to 45±5
   MAE III 30±5 to 45±4
   MOCA (Montreal Cognitive Assessment) 76±8 to 86±6

3. Improvement in cardiac diastolic dysfunction:
   Male mice (30-35 months old) were studied in 2 groups—one group was fed chow diet (control group-CON) and the feed of the other group was supplemented with cysteine plus glycine (NacGly). Noninvasive measurements of aortic outflow, transmitral flow, aortic stiffness, and echocardiographic measures of Left Ventricular and Atrial anatomy and function were compared before and after seven weeks on diet (n=4 in each group. NacGly mice showed significant improvement in the transmitral flow parameters compared to control which did not change. NacGly mice also significantly improved isovolumic relaxation time (Con 23.1+2.5 vs NacGly 19.2+0.7 msec. p<0.05), isovolumic contraction time (Con 26.3+4.6 vs NacGly 13.9+0.3 msec, p<0.05), peak Early filling velocity (Con 67+4 vs NacGly 78+5 cm/sec, p<0.05). The conclusions of this study are that dietary supplementation with cysteine (as n-acetylcysteine) and Glycine improve diastolic function in old mice.

4. Liver fat in HIV patient: Liver fat content was studied by MRI before and after supplementation of cysteine and glycine for 12 weeks in 1 subject. The results showed the following:
   Liver fat by MRI
   Right Anterior Lobe (%)
   Right Posterior Lobe (%)
   Baseline (before supplement)
   7.0+/−0.9%
   8.5+/−1.2%
   Follow up (after supplement)
   5.0+/−1.1%
   6.0+/−1.2%

5. Liver fat in diabetic mice: Two groups of mice were studied after 1 year of exposure to severe uncontrolled diabetes. From the time of induction of diabetes, one group (treatment group) received supplementation with cysteine (as n-acetylcysteine) and glycine, whereas the other (control) group received a control feed which was isonitrogenous and isocaloric to the first group. Histological evaluation showed 95-100% prevalence of fatty-liver in the control group receiving the isonitrogenous/isocaloric diet, whereas the treatment group consuming the cysteine/glycine diet had a prevalence of only 2-5% of fatty liver. Quantification of liver fat showed a significantly lower amount in the treated mice.

5. Muscle protein breakdown: Muscle protein breakdown was studied using the tracer 3-methylhistidine before and after 12 weeks of supplementation with cysteine (as n-acetylcysteine) and glycine in 3 older HIV patients. Results showed a significant decline in myofibrillar protein breakdown. These data suggest that improving glutathione with cysteine and glycine in aging could lower muscle breakdown and combat sarcopenia.

Myofibrillar muscle protein breakdown rate:
Before supplementation: 203±59 mg/kgLBM/h
After supplementation: 137±15 mg/kgLBM/h Example 10

Examples of Supplementation with N-Acetylcysteine and Glycine

In mouse studies, the action of n-acetylcysteine and glycine improves mitochondrial function and muscle strength in old mice, and in specific embodiments this occurs via glutathione. In some embodiments, supplementation of n-acetylcysteine and glycine lowers liver fat in mice.

In particular aspects, supplementation of n-acetylcysteine and glycine in HIV patients improves mild neurocognitive deficits in HIV infected patients, improves muscle strength and exercise capacity; and/or restores glutathione to age matched controls.

In certain embodiments, in an ongoing study in geriatric humans, supplementation of n-acetylcysteine and glycine improves cognitive deficits within at least 4 weeks.

Example 11

HIV Physical and Neurocognitive Data

HIV infected patients are reported to have accelerated aging with a decline in physical function. HIV patients are also reported to have significant impairment of cognitive function. To evaluate the impact of cysteine and glycine supplementation, we studied 8 HIV patients before and after 12 weeks of supplementation with cysteine (as n-acetylcysteine) and glycine, and the comparator control groups were 8 HIV negative humans matched for age, gender and BMI. The outcome measures included physical function (gait speed) and neurocognitive function (Trailmaking tests and MAEIII).

The results showed that compared to non-HIV controls, HIV infected patients had significantly lower gait speed (1.3±0.1 vs. 1.06±0.04 m/s, $p<0.001$), and significant cognitive impairment as measured by the Trailmaking test A (34.6±3.6 vs. 62.6±6.1 seconds, $p<0.01$) and Trailmaking test B (53.8±7.2 vs. 117.5±5.0 seconds, $p<0.01$), and by the Multilingual Aphasic Examination III (41.0±3.5 vs. 28.9±3.2 words, $p<0.01$). After 12-weeks of supplementation, compared to pre-supplemented levels the gait speed of HIV patients had recovered (1.06±0.04 vs. 1.30±0.04 m/s, $p<0.01$) to levels which were similar and comparable to that in HIV negative controls, suggesting that cysteine and glycine supplementation could reverse accelerated aging in HIV patients. This is further supported by a significant increase in cognitive function (pre-supplemented vs post-supplemented levels) as seen by the improvement in scores of Trailmaking tests A (62.6±6.1 vs 46.4±4.4 vs. seconds, $p<0.01$) and B (117.5±5.0 vs 69.8±5.4 vs. seconds, $p<0.01$), and MAE III (28.9±3.2 vs. 34.6±2.0 words, $p<0.01$).

Conclusions: Supplementation of cysteine and glycine reverses glutathione deficiency in HIV patients, and reverses functional decline and cognitive function. Collectively these data support the indication that cysteine and glycine supplementation reverses accelerated aging in HIV-infected patients.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

PUBLICATIONS

Al-Turk W A, Stohs S J, el-Rashidy F H, Othman S. Changes in glutathione and its metabolizing enzymes in human erythrocytes and lymphocytes with age. J Pharm Pharmacol 1987; 39:13-6.

Bella D L, Hahn C, Stipanuk M H. Effects of nonsulfur and sulfur amino acids on the regulation of hepatic enzymes of cysteine metabolism. Am J Physiol 1999; 277:E144-53.

Boirie Y, Gachon P, Beaufrere B. Splanchnic and whole-body leucine kinetics in young and elderly men. Am J Clin Nutr 1997; 65:489-95.

Campisi A, Di Giacomo C, Russo A, et al. Antioxidant systems in rat lens as a function of age: effect of chronic administration of vitamin E and ascorbate. Aging (Milano) 1999; 11:39-43.

Campbell W W, Crim M C, Dallal G E, Young V R, Evans W J. Increased protein requirements in elderly people: new data and retrospective reassessments. Am J Clin Nutr 1994; 60:501-9.

Castorina C, Campisi A, Di Giacomo C, Sorrenti V, Russo A, Vanella A. Lipid peroxidation and antioxidant enzymatic systems in rat retina as a function of age. Neurochem Res 1992; 17:599-604.

Cresenzi C L, Lee J I, Stipanuk M H. Cysteine is the metabolic signal responsible for dietary regulation of hepatic cysteine dioxygenase and glutamate cysteine ligase in intact rats. J Nutr 2003; 133:2697-702.

Erden-Inal M, Sunal E, Kanbak G. Age-related changes in the glutathione redox system. Cell Biochem Funct 2002; 20:61-6.

Farooqui M Y, Day W W, Zamorano D M. Glutathione and lipid peroxidation in the aging rat. Comp Biochem Physiol B 1987; 88:177-80.

Fereday A, Gibson N R, Cox M, Pacy P J, Millward D J. Protein requirements and ageing: metabolic demand and efficiency of utilization. Br J Nutr 1997; 77:685-702.

Fidelus R K, Tsan M F. Glutathione and lymphocyte activation: a function of ageing and auto-immune disease. Immunology 1987; 61:503-8.

Furukawa T, Meydani S N, Blumberg J B. Reversal of age-associated decline in immune responsiveness by dietary glutathione supplementation in mice. Mech Ageing Dev 1987; 38:107-17.

Grimble R F, Jackson A A, Persaud C, Wride M J, Delers F, Engler R. Cysteine and glycine supplementation modulate the metabolic response to tumor necrosis factor alpha in rats fed a low protein diet. J Nutr 1992; 122:2066-73.

Hashimoto K, Takasaki W, Yamoto T, Manabe S, Sato I, Tsuda S. Effect of glutathione (GSH) depletion on DNA damage and blood chemistry in aged and young rats. J Toxicol Sci 2008; 33:421-9.

Jackson A A, Gibson N R, Lu Y, Jahoor F. Synthesis of erythrocyte glutathione in healthy adults consuming the safe amount of dietary protein. Am J Clin Nutr 2004; 80:101-7.

Jahoor F, Wykes L J, Reeds P J, Henry J F, del Rosario M P, Frazer M E. Protein-deficient pigs cannot maintain reduced glutathione homeostasis when subjected to the stress of inflammation. J Nutr 1995; 125:1462-72.

Lang C A, Naryshkin S, Schneider D L, Mills B J, Lindeman R D. Low blood glutathione levels in healthy aging adults. J Lab Clin Med 1992; 120:720-5.

Liu R, Choi J. Age-associated decline in gamma-glutamylcysteine synthetase gene expression in rats. Free Radic Biol Med 2000; 28:566-74.

Liu H, Wang H, Shenvi S, Hagen T M, Liu R M. Glutathione metabolism during aging and in Alzheimer disease. Ann N Y Acad Sci 2004; 1019:346-9.

Loguercio C, Taranto D, Vitale L M, Beneduce F, Del Vecchio Blanco C. Effect of liver cirrhosis and age on the glutathione concentration in the plasma, erythrocytes, and gastric mucosa of man. Free Radic Biol Med 1996; 20:483-8.

Lyons J, Rauh-Pfeiffer A, Yu Y M, et al. Blood glutathione synthesis rates in healthy adults receiving a sulfur amino acid-free diet. Proc Natl Acad Sci USA 2000; 97:5071-6.

Matsubara L S, Machado P E. Age-related changes of glutathione content, glutathione reductase and glutathione peroxidase activity of human erythrocytes. Braz J Med Biol Res 1991; 24:449-54.

Morais J A, Gougeon R, Pencharz P B, Jones P J, Ross R, Marliss E B. Whole-body protein turnover in the healthy elderly. Am J Clin Nutr 1997; 66:880-9.

Rahman, I., Aruna Kodel, Saibal K Biswas. Assay for quantitative determination of glutathione and glutathione disulfide levels using enzymatic recycling method. Nature Protocols 2006; 1(6): 3159-3165.

Rebrin I, Sohal R S. Pro-oxidant shift in glutathione redox state during aging. Adv Drug Deliv Rv 2008; 60:1545-52.

Reid M, Jahoor F. Methods for measuring glutathione concentration and rate of synthesis. Curr Opin Clin Nutr Metab Care 2000; 3:385-90.

Rikans L E, Hornbrook K R. Lipid peroxidation, antioxidant protection and aging. Biochim Biophys Acta 1997; 1362:116-27.

Rizvi S I, Maurya P K. Markers of oxidative stress in erythrocytes during aging in humans. Ann N Y Acad Sci 2007; 1100:373-82.

Samiec P S, Drews-Botsch C, Flagg E W, et al. Glutathione in human plasma: decline in association with aging, age-related macular degeneration, and diabetes. Free Radic Biol Med 1998; 24:699-704.

Stohs S J, Lawson T, Al-Turk W A. Changes in glutathione and glutathione metabolizing enzymes in erythrocytes and lymphocytes of mice as a function of age. Gen Pharmacol 1984; 15:267-70.

Sweeney M H, Truscott R J. An impediment to glutathione diffusion in older normal human lenses: a possible precondition for nuclear cataract. Exp Eye Res 1998; 67:587-95.

Toroser D, Sohal R S. Age-associated perturbations in glutathione synthesis in mouse liver. Biochem J 2007; 405:583-9.

Young V R. Amino acids and proteins in relation to the nutrition of elderly people. Age Ageing 1990; 19:S10-24.

Although the present invention and its advantages have been described in detail, it should be understood that various changes, substitutions and alterations can be made herein without departing from the invention as defined by the claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the claims are intended to include within their scope such processes, machines, manufacture, compositions of matter, means, methods, or steps.

The claimed invention is:

1. A method of treating an individual for a medical condition or physical state, the method comprising providing to the individual an effective amount of a composition comprising N-acetylcysteine and a functional derivative of glycine,
wherein the functional derivative of glycine is selected from the group consisting of D-Allylglycine; N-[Bis(methylthio)methylene]glycine methyl ester; Boc-allyl-Gly-OH (dicyclohexylammonium) salt; Boc-D-Chg-OH; Boc-Chg-OH; (R)—N-Boc-(2'-chlorophenyl)glycine; Boc-L-cyclopropylglycine; (R)—N-Boc-4-fluorophenylglycine; Boc-D-propargylglycine; Boc-(S)-3-thienylglycine; Boc-(R)-3-thienylglycine; D-α-Cyclohexylglycine; L-α-Cyclopropylglycine; N-(2-fluorophenyl)-N-(methylsulfonyl)glycine; N-(4-fluorophenyl)-N-(methylsulfonyl)glycine; Fmoc-N-(2,4-dimethoxybenzyl)-Gly-OH; N-(2-Furoyl)glycine; L-α-Neopentylglycine; D-Propargylglycine; sarcosine; Z-α-Phosphonoglycine trimethyl ester; and a mixture thereof;
wherein the medical condition or physical state is selected from the group consisting of
muscle loss;
deleterious effects of weightlessness;
osteoporosis;
hypertension;
polycystic ovary syndrome (PCOS);
coronary artery disease;
myocardial damage after stress;
insufficient immunity following vaccination;
ototoxicity;
dizziness; and
a combination thereof;
wherein the composition has at least one formulation selected from the group consisting of (i) the N-acetylcysteine is at least 2 wt. % of the composition and (ii) the functional derivative of glycine is at least 8 wt. % of the composition.

2. The method of claim 1, wherein the functional derivative of glycine and the N-acetylcysteine are provided to the individual in the same composition.

3. The method of claim 1, wherein the functional derivative of glycine and the N-acetylcysteine are provided to the individual in different compositions.

4. The method of claim 1, wherein the functional derivative of glycine and the N-acetylcysteine are provided orally to the individual.

5. A method of treating an individual for a medical condition or physical state, the method comprising providing to the individual an effective amount of a composition comprising N-acetylcysteinylglycine,
- wherein the medical condition or physical state is selected from the group consisting of
- muscle loss;
- deleterious effects of weightlessness;
- osteoporosis;
- hypertension;
- polycystic ovary syndrome (PCOS);
- coronary artery disease;
- myocardial damage after stress;
- insufficient immunity following vaccination;
- ototoxicity;
- dizziness; and
- a combination thereof;
- wherein the N-acetylcysteinylglycine is at least 2 wt. % of the composition.

6. The method of claim 5, wherein the N-acetylcysteinylglycine is at least 8 wt. % of the composition.

\* \* \* \* \*